United States Patent
Lai

(10) Patent No.: US 8,181,542 B2
(45) Date of Patent: May 22, 2012

(54) PULLOUT MECHANISM FOR BIOSENSOR

(76) Inventor: Ming-Hsiao Lai, Chang-Hua Hsien (TW)

(*) Notice: Subject to any disclaimer, the term of this patent is extended or adjusted under 35 U.S.C. 154(b) by 303 days.

(21) Appl. No.: 12/687,744

(22) Filed: Jan. 14, 2010

(65) Prior Publication Data

US 2011/0167935 A1   Jul. 14, 2011

(51) Int. Cl.
*G01N 1/00* (2006.01)
(52) U.S. Cl. .......................................................... 73/863
(58) Field of Classification Search ........................ None
See application file for complete search history.

(56) References Cited

U.S. PATENT DOCUMENTS 7,661,325 B2 * 2/2010 Nishina ........................... 73/863

* cited by examiner

*Primary Examiner* — Robert R Raevis
(74) *Attorney, Agent, or Firm* — Egbert Law Offices PLLC

(57) ABSTRACT

A pullout mechanism for a biosensor, wherein the pullout mechanism includes a permanent seat, a sliding seat, a resetter and a push type brake seat. The sliding seat is set into the sliding seat space of the permanent seat in a sliding state. A resetter is arranged between the permanent seat and the sliding seat, enabling resetting of the sliding seat. A push type brake seat is arranged laterally onto the casing. The push type brake seat includes a pushing portion and a driving end. The driving end can penetrate the threading portion of the permanent seat. When the pushing portion is pressed, said driving end can push the driven end of the sliding seat to control the state of the sliding seat, allowing for automatic pullout of the specimen in the specimen inserting portion, and improving the ease of operation with stronger applicability.

5 Claims, 7 Drawing Sheets

PULLOUT MECHANISM FOR BIOSENSOR

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates generally to a biosensor, and more particularly to an innovative one which is equipped with a push type pullout mechanism.

2. Description of Related Art Including Information Disclosed Under 37 CFR 1.97 and 37 CFR 1.98

With the progress of biosensing technology, some medical detection procedures that have to be performed by specialists in big hospitals or labs can be streamlined, and conducted individually by unskilled personnel or inspectors.

The medical instruments and apparatuses can be carried with the users and utilized conveniently due to the development of test specimens and simplification of instruments. In this way, the results can be easily obtained if the test samples are adsorbed or coated onto specific test specimens by the user, and then inserted into the portable analyzer. To prevent the user from pulling out manually the specimens with test samples after completion of detection, a diagnoser with pullout function has been developed in the industry; yet, there exist some structural shortcomings of the diagnoser with pullout function. These include quantity of structural members and convenience of operation, which require further efforts to make improvements by the industry.

Thus, to overcome the aforementioned problems of the prior art, it would be an advancement if the art to provide an improved structure that can significantly improve the efficacy.

Therefore, the inventor has provided the present invention of practicability after deliberate experimentation and evaluation based on years of experience in the production, and development of related products.

BRIEF SUMMARY OF THE INVENTION

The enhanced efficacy of the present invention is as follows:

Based on the unique configuration of the present invention that the "pullout mechanism" is mainly characterized by the pullout mechanism that is fitted with said push type brake seat, the sliding seat can be driven by said push type brake seat to push the specimen. The pullout mechanism can be used to control the pullout of the specimen by means of pushing. This eliminates the possibility of manual contact with the specimen adhered with test samples, thus ensuring the personal health and safety during detection process. Moreover, the push type pattern is particularly suitable for the operation when holding manually the biosensor. This could save the operational cost and improve the ease of operation with improved applicability.

Although the invention has been explained in relation to its preferred embodiment, it is to be understood that many other possible modifications and variations can be made without departing from the spirit and scope of the invention as hereinafter claimed.

DETAILED DESCRIPTION OF THE INVENTION

Figure 1:
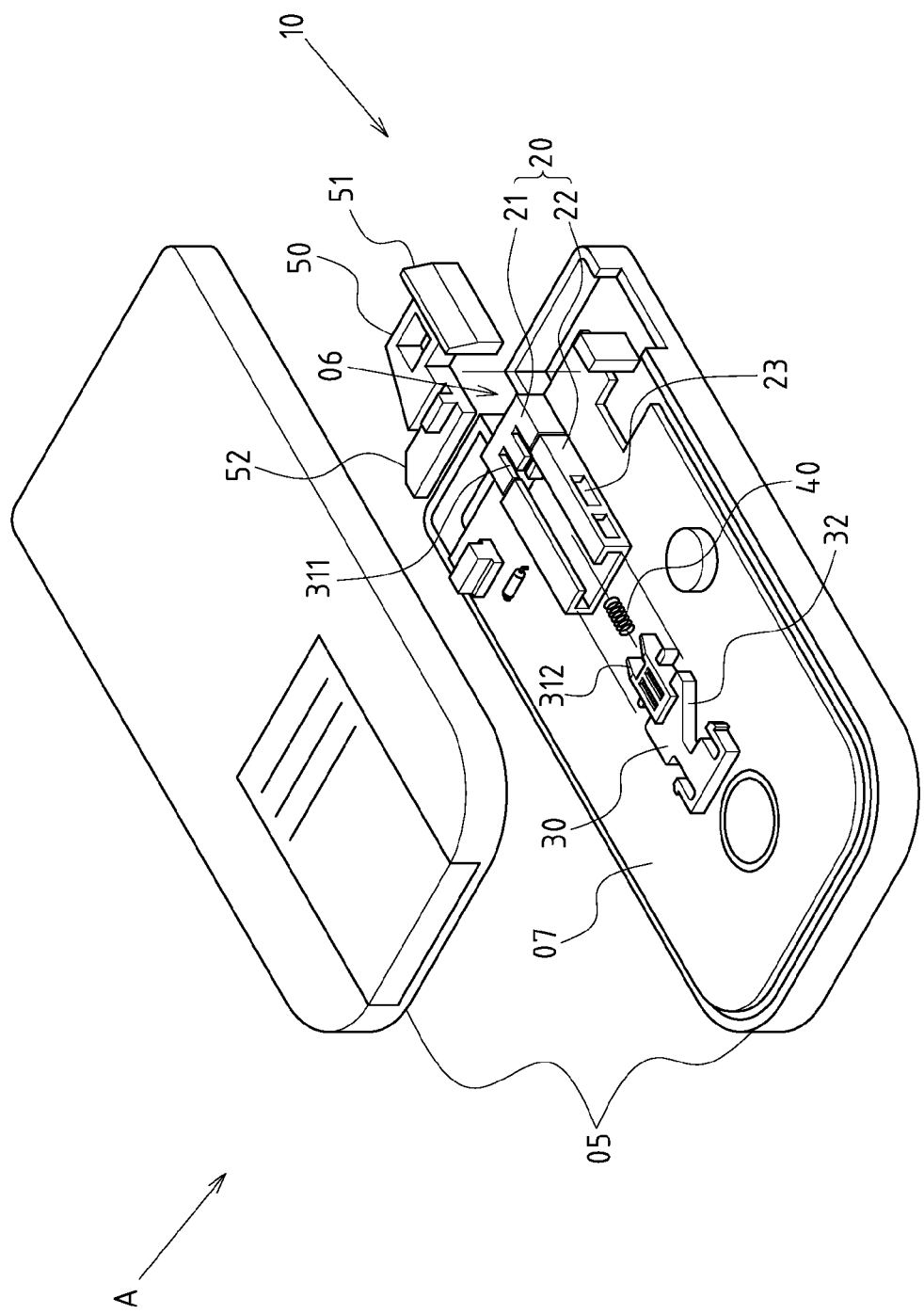
FIG. 1 shows an exploded perspective view of the preferred embodiment of the present invention.
Figure 2:
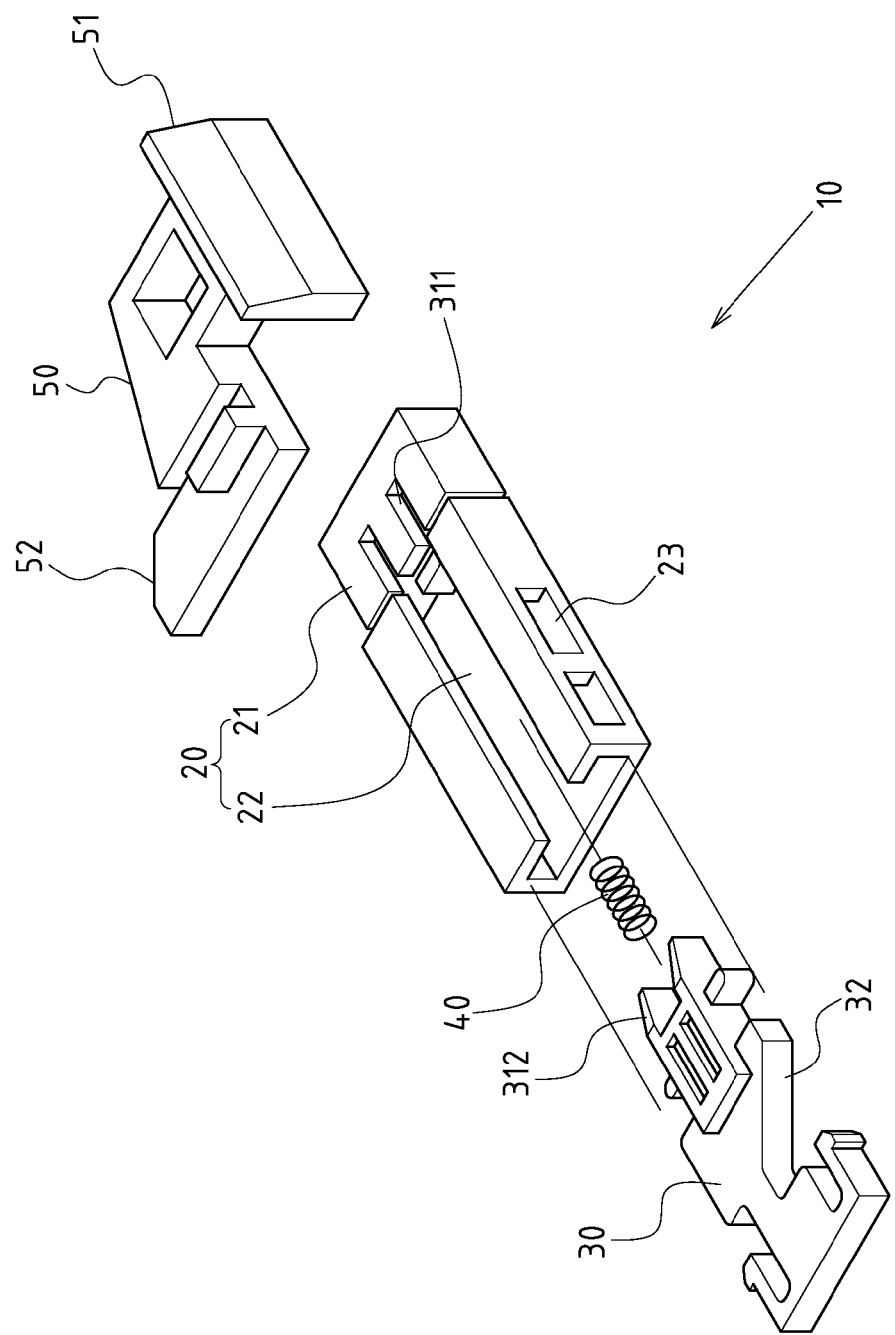
FIG. 2 shows a perspective view of the pullout mechanism of the present invention.
Figure 3:
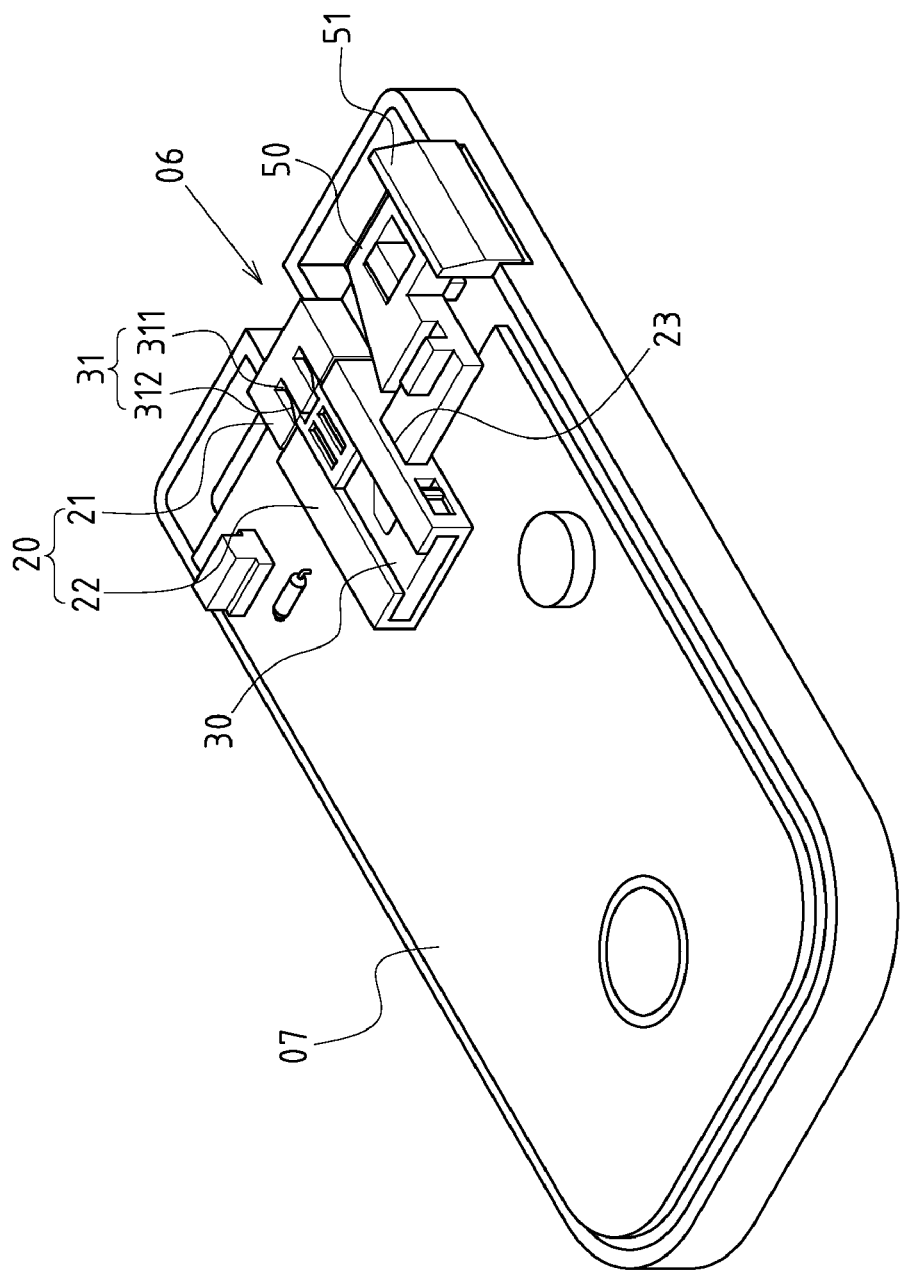
FIG. 3 shows a perspective view of the preferred embodiment of the present invention.

FIGS. 1-4 depict preferred embodiments of a pullout mechanism of biosensor of the present invention, which are provided for only explanatory objective for patent claims. Said biosensor A comprises a casing 05, onto one end of which a specimen insertion end 06 is formed. The casing 05 is provided with a circuit board 07, a display panel and a control button, of which said display panel and control button are located at the bottom of the casing 05 as illustrated in FIG. 1. Said pullout mechanism 10 is mounted correspondingly to the specimen insertion end 06, enabling automatic pullout of the specimens from the specimen insertion end 06; the pullout mechanism 10 includes a permanent seat 20, assembled fixedly into the casing 05 (note: the permanent seat 20 of the preferred embodiment is assembled onto the circuit board 07). It includes a specimen inserting portion 21 and a sliding seat space 22 arranged vertically; a threading portion 23 is set laterally on the sliding seat space 22; when the specimen 60 is inserted into the specimen inserting portion 21, it is connected electrically with the circuit board 07, allowing the detection results of the specimen 60 to be displayed on the display panel by the biosensor A.

A sliding seat 30 is set into the sliding seat space 22 of the permanent seat 20 in a sliding state; the sliding seat 30 and the permanent seat 20 are mated to form a specimen pusher 31, permitting to push the specimen 60 already inserted into the specimen inserting portion 21. The sliding seat 30 is provided with a driven end 32.

A resetter 40 made of spring is arranged between the permanent seat 20 and the sliding seat 30, enabling the sliding seat 30 to push the resetter 40 for recovering the elastic force.

A push type brake seat 50 is arranged laterally onto the casing 05. It includes a pushing portion 51 and a driving end 52. The driving end 52 can penetrate the threading portion 23 of the permanent seat 20. When the pushing portion 51 is pressed, said driving end 52 can push the driven end 32 of the sliding seat 30 to control the state of the sliding seat 30, allowing automatic pullout of the specimen 60 in the specimen inserting portion 21. In this way, it is possible to maintain the safety and health of the user since no specimen 60 adhered with test samples is exposed to the user after completion of detection.

Of which, the specimen pusher 31 includes a guide slot 311 and a specimen push rod 312. The guide slot 311 is arranged within the specimen inserting portion 21 of the permanent seat 20, whilst the specimen push rod 312 is arranged at one end of the sliding seat 30. Said specimen push rod 312 can slide within the guide slot 311.

Figure 4:
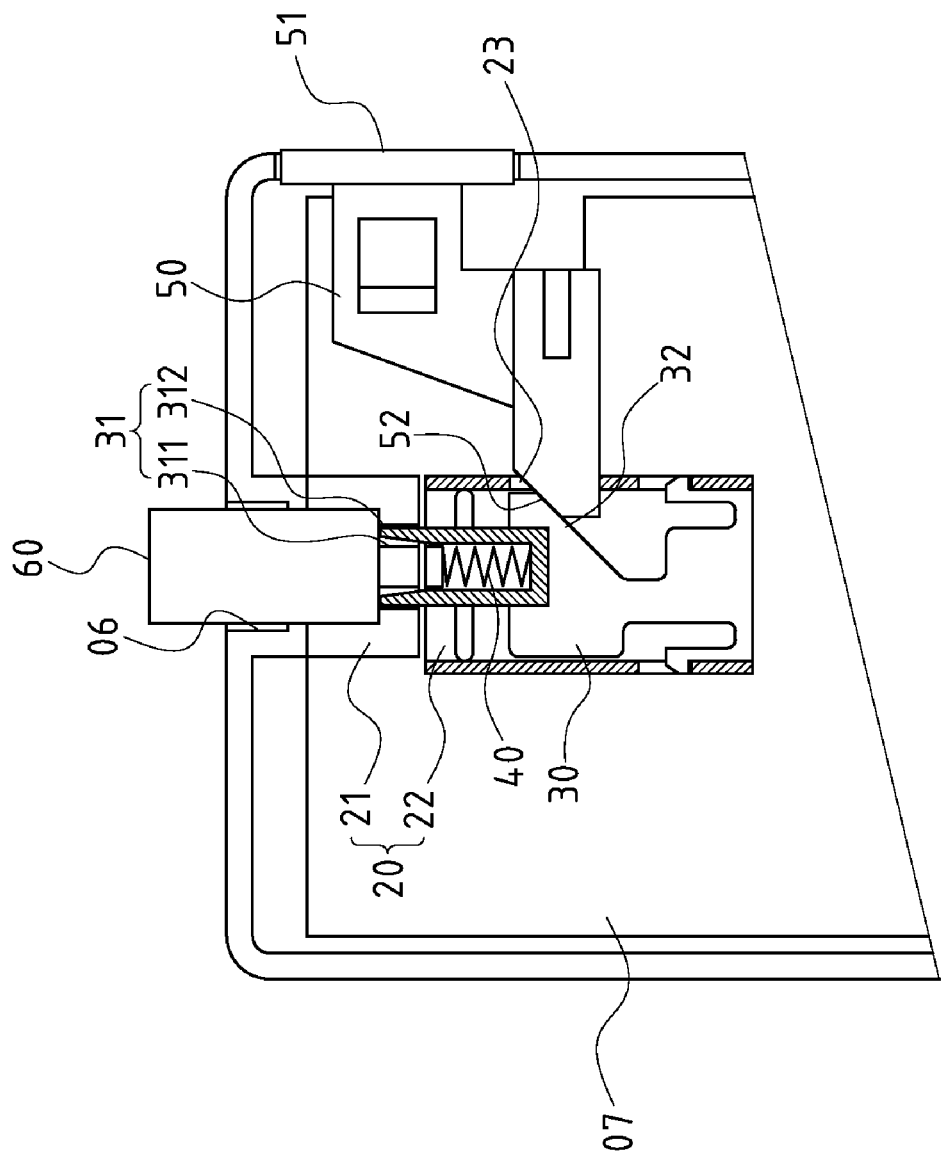
FIG. 4 shows a schematic view of the present invention that specimen is inserted into the preferred embodiment.
Figure 5:
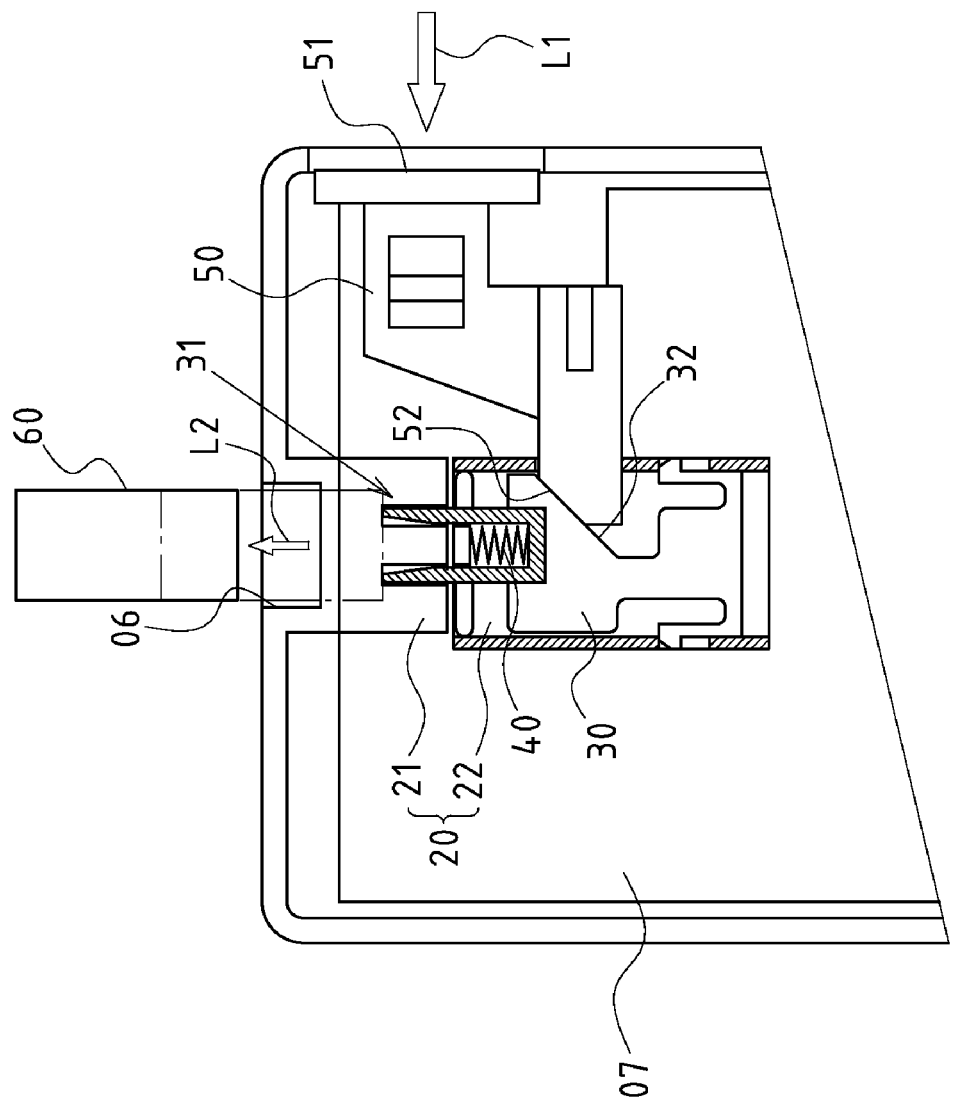
FIG. 5 shows another schematic view of the preferred embodiment of the present invention.

Referring to FIGS. 4 and 5, the driven end 32 of the sliding seat 30 and the driving end 52 of the push type brake seat 50 can be set into a mated oblique pattern. Referring to FIG. 5, the oblique pushing action of the driven end 32 and the driving end 52 permits outward shift of the sliding seat 30, so that the specimen 60 already inserted into the specimen inserting portion 21 can be pulled out (shown by arrow L2); the resetter 40 is set close to the specimen inserting portion 21, permitting to push elastically the sliding seat 30 towards the interior of the sliding seat space 22 for its inward resetting. When the pushing force of the driving end 52 of the push type brake seat 50 against the driven end 32 of the sliding seat 30 is released, the sliding seat 30 can be reset inwards with the elastic pushing force of the resetter 40 (shown in FIG. 4).

Based on above-specified structural configuration, the present invention is operated as follows:

As for the structural configuration that said resetter 40 is set close to the specimen inserting portion 21 of the permanent seat 20, referring to FIGS. 1-5 of the preferred embodiments, the driven end 32 of the sliding seat 30 and the driving end 52 of the push type brake seat 50 can be set into a mated oblique pattern. With this configuration, after a specimen 60 is fed into the specimen inserting portion 21 of the permanent seat 20 from the specimen insertion end 06 of the casing 05 and the detection is finished, users can push the pushing portion 51 of the push type brake seat 50 (shown by arrow L1 in FIG. 5) to shift the driving end 52 of the push type brake seat 50, so that the driving end 52 and the driven end 32 are mated in the oblique surface to push the sliding seat 30. In such a case, the specimen 60 is pulled out under the pushing force of the specimen push rod 312 of the sliding seat 30 (shown by arrow L2 in FIG. 5), thus realizing automatic pullout of the specimen 60 already inserted into the specimen inserting portion 21. Meanwhile, the sliding seat 30 also pushes the resetter 40 to accumulate the elastic force; when the force applied to the pushing portion 51 of the push type brake seat 50 is removed, the resetter 40 is released to realize automatic resetting of the sliding seat 30.

Figure 6:
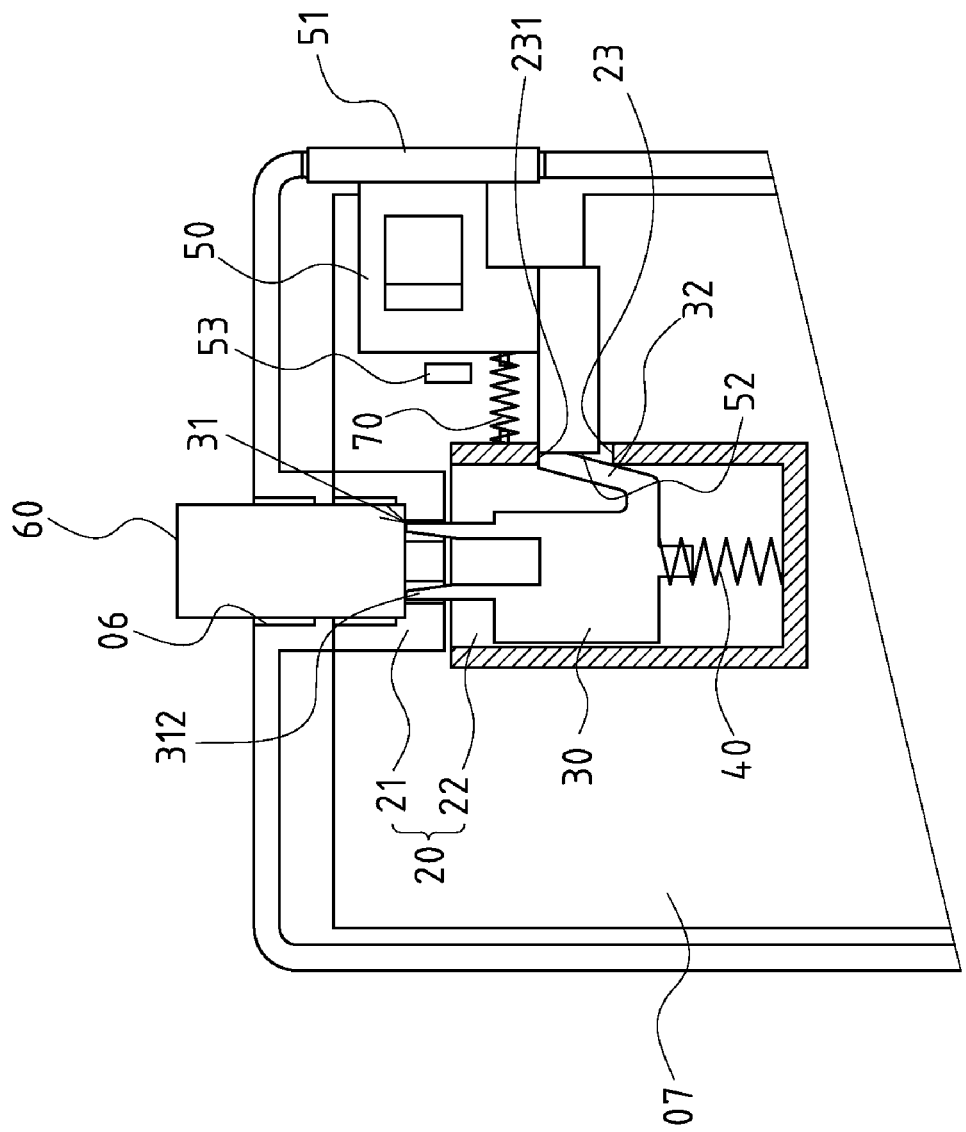
FIG. 6 shows another schematic view of the present invention that specimen is inserted into another preferred embodiment.
Figure 7:
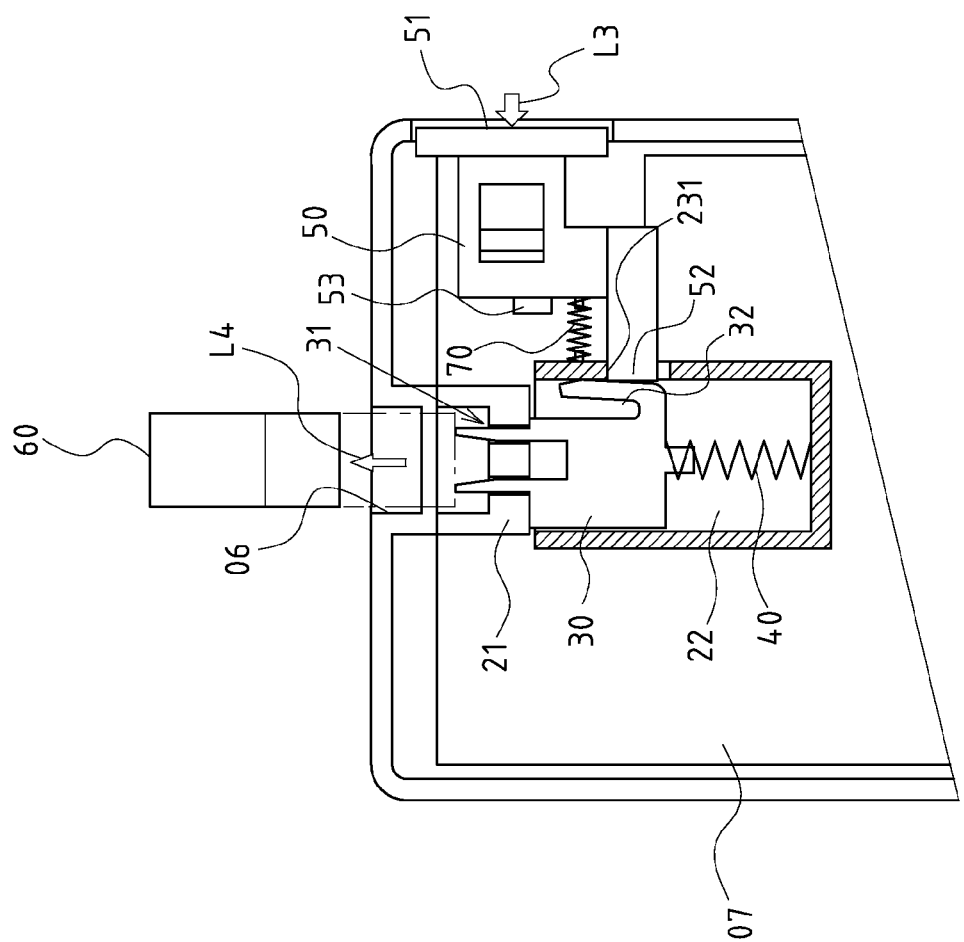
FIG. 7 shows yet another schematic view of another preferred embodiment of the present invention.

Referring also to FIGS. 6 and 7, an abutting side 231 is also formed on one end of the threading portion 23 of the sliding seat space 22. The driven end 32 of said sliding seat 30 is designed into an elastic slanting arm. The resetter 40 of the preferred embodiment is set far from the specimen inserting portion 21, so that the sliding seat 30 is pushed elastically towards the exterior of the sliding seat space 22, enabling outward resetting of the sliding seat 30. When the specimen 60 is inserted into the specimen inserting portion 21, the specimen push rod 312 of said sliding seat 30 will be pushed, and the sliding seat 30 is under a sliding state. Moreover, one end of the driven end 32 is blocked by the abutting side 231, and the resetter 40 is pressed to accumulate elastic force. With this configuration, when the specimen 60 is inserted into the specimen inserting portion 21, the driven end 32 of elastic slanting arm pattern can be snapped into the abutting side 231, so the resetter 40 is pressed to accumulate the elastic force (shown in FIG. 6). As shown by arrow L3 in FIG. 7, when the pushing portion 51 is pressed, the driving end 52 can push the driven end 32 of the sliding seat 30 to be disengaged from the abutting side 231, so that the sliding seat 30 is elastically pushed outwards by the resetter 40 and the specimens in the specimen inserting portion can be automatically pulled out (shown by arrow L4 in FIG. 7).

Furthermore, an elastic supporting member 70 (e.g. spring) is arranged between the exterior of the permanent seat 20 and the push type brake seat 50. Said elastic supporting member 70 can support elastically the push type brake seat 50 to remove the loosening of the push type brake seat 50 generated from the assembly clearance, thus realizing the compactness and robustness of push type brake seat 50 in the operating condition. Referring to FIG. 7, a limiter 53 is arranged onto a preset location of the circuit board 07 or the casing 05. The limiter 53 is of a protruding or bulging pattern, and used for limiting securely the push type brake seat 50 in its maximum pressing state.

I claim:

1. An apparatus comprising:
    a casing having a specimen insertion end at one end thereof; and
    a pullout mechanism positioned at said specimen insertion end, said pullout mechanism suitable for allowing a specimen to be pulled out of said specimen insertion end, said pullout mechanism comprising:
        a permanent seat fixedly mounted into said casing, said permanent seat having a specimen insertion portion and a seating space, said permanent seat having a slot on a side thereof, said slot opening to said seating space;
        a sliding seat slidably positioned in said seating space, said sliding seat being mated to said permanent seat so as to form a specimen pusher, said sliding seat having a driven end;
        a resetter arranged between said permanent seat and said sliding seat so as to allow a resetting of said sliding seat; and
        a brake seat positioned at a side of said casing, said brake seat having a pushing portion and a driving end, said driving end extending into said slot of said permanent seat, said pushing portion being pushable so as to urge said driving end to push said driven end of said sliding seat so as to cause a removal of the specimen insertion portion.

2. The apparatus of claim 1, said driven end of said sliding seat and said driving end of said brake seat arranged in a mated oblique angle, said resetter positioned adjacent said specimen insertion portion so as to elastically urge said sliding seat toward an interior of said seating space when said driving end does not push said driven end of said sliding seat.

3. The apparatus of claim 1, said slot of said permanent seat having an abutting side at one end thereof, said driven end of said sliding seat having an elastic slanting arm, said resetter being spaced from said specimen insertion portion so as to urge said sliding seat toward an exterior of said seating space, said driven end of said sliding seat being snappable onto said abutting side, said driving end pushing said driven end of said sliding seat so as to disengage from said abutting side such that said sliding seat is elastically pushed outwardly by said resetter.

4. The apparatus of claim 1, further comprising:
    an elastic supporting member arranged between an exterior of said permanent seat and said brake seat.

5. The apparatus of claim 1, said casing having a circuit board therein, the apparatus further comprising:
    a limiter positioned at a location adjacent said circuit board so as to limit a position of said brake seat.

* * * * *